United States Patent [19]

Brooks, Jr.

[11] 4,018,807
[45] Apr. 19, 1977

[54] SYNTHESIS OF AROMATIC SULFUR-OXYGEN TRANSITION METAL COMPLEXES

[75] Inventor: Houston George Brooks, Jr., Somerset, N.J.

[73] Assignee: American Cyanamid Company, Stamford, Conn.

[22] Filed: July 25, 1975

[21] Appl. No.: 599,225

[52] U.S. Cl. .................. 260/439 R; 260/429 R; 260/429 K; 260/429.5; 260/429.9; 260/430; 260/433; 260/435 R; 260/438.1; 260/438.5 R
[51] Int. Cl.$^2$ ..................................... C07F 15/04
[58] Field of Search ....... 260/429 R, 439 R, 429 K, 260/438.5, 429.5, 429.9, 435, 433, 430, 438.1

[56] References Cited
UNITED STATES PATENTS

| | | | |
|---|---|---|---|
| 2,490,717 | 12/1949 | Steiger | 260/439 R X |
| 3,162,688 | 12/1964 | Thigpen et al. | 260/439 R X |
| 3,202,688 | 8/1965 | Matson | 260/429 R |
| 3,775,484 | 11/1973 | Ciaudelli | 260/429.9 X |

OTHER PUBLICATIONS

Chemical Abstracts, v. 77, 19416b (1972).
Balch, J.A.C.S., v. 91, pp. 1948–1953 (1969).

*Primary Examiner*—Helen M. S. Sneed
*Attorney, Agent, or Firm*—John L. Sullivan

[57] ABSTRACT

Transition metal complexes of mono- and polynuclear aromatic o-hydroxymercaptans are produced in high yield and purity directly from o-hydroxythiocyanates by reaction thereof with water-soluble transition metal salts. When incorporated into plastic lenses, the complexes afford eye protection against laser radiation.

9 Claims, No Drawings

SYNTHESIS OF AROMATIC SULFUR-OXYGEN TRANSITION METAL COMPLEXES

This invention relates to a method for the synthesis of transition metal complexes of aromatic 0-hydroxymercaptans. More particularly, it relates to a method for the synthesis of mono- or polynuclear aromatic sulfur-oxygen transition metal complexes, represented generally as a complex having the structure (I):

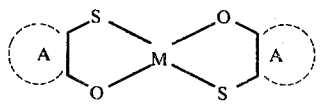

wherein M is a transition metal and A represents a mono- or polycyclic aromatic ring system.

Certain metal complexes of aromatic 0-hydroxymercaptans, for example, the nickel and cobalt complexes of (I) wherein A is a phenanthrene ring system, possess near infrared spectral properties; that is, they absorb in the region from about 1000—1600 nanometers. Incorporated into certain plastic materials of optical quality and fabricated into spectacles or face shieds, they provide eye protection against laser radiation.

Previous attempts to prepare the transition metal complexes of o-hydroxymercaptans have generally involved synthesis of the o-hydroxythiocyanate, conversion of the o-hydroxythiocyanate to the corresponding 0-hydroxy disulfide, followed by the reduction thereof to the o-hydroxymercaptan. The reduction step is ordinarily associated with yield reducing side reactions, primarily re-oxidation to the disulfide, resulting in generally poor yields. The following reaction sequence generally illustrates the conventional synthesis of the metal complexes:

yields of high purity product, directly from an o-hydroxythiocyanate by reaction thereof with a water soluble transition metal salt.

The method of the present invention has significant advantages over previous methods in that the method avoids conversion of the thiocyanate to the disulfide and reduction of the disulfide to the corresponding thiol. Moreover, the complex forming reaction is essentially quantitative and purity is generally very high. The method can be illustrated generally as follows:

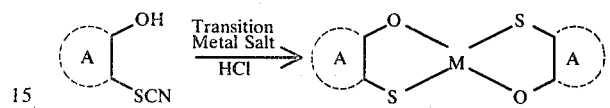

The method is generally applicable to any aromatic o-hydroxythiocyanate, either monocyclic or polycyclic. Representative o-hydroxythiocyanates include o-hydroxyphenylthiocyanate, 2-hydroxy-1-naphthyl thiocyante, 9-hydroxy-10-thiocyanatophenanthrene, 2,3-dimethoxy-9-hydroxy-10phenanthrenethiocyante, 5-hydroxy-6-benzo[c]phenanthrenethiocyanate, and the like.

Preparation of the appropriate o-hydroxythiocyanate is accomplished by conventional organic chemical means. Introduction of a thiocyanate group into the molecule can be accomplished, for example, by the procedure described in Organic Syntheses, Coll. Vol. II (Blatt, Ed.), page 574, publ. John Wiley, N.Y., N.Y., using ammonium thiocyanate and bromine. Sodium and potassium thiocyanate may also be used.

The metals useful in preparing the complexes of this invention are those ordinarily classified as transition metals, and include elements 21 thru 30 (scandium thru zinc), 39 thru 48 (yttrium thru cadmium) and 72 thru 80 (hafnium thru mercury), and particularly the

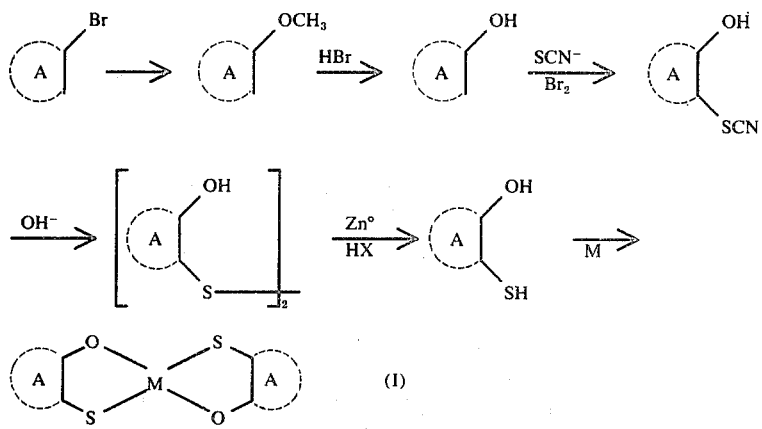

The reactions illustrated above are individually well known and conventional.

There is a need, therefore, for a method of improving the overall yield of transition metal complexes of o-hydroxymercaptans. It is an object of the present invention to provide a novel method for the synthesis of transition metal complexes of mono- and polynuclear aromatic 0-hydroxymercaptans.

In accordance with the above stated object, I have discovered a novel, generally applicable method for the synthesis of transition metal complexes of mono- and polynuclear aromatic o-hydroxymercaptans, in high metals titanium, chromium, manganese, iron, cobalt, nickel, copper, zinc, cadmium, lead, silver, mercury and platinum. The metal salts used to prepare the complexes should be soluble in water to some extent.

The complex forming reaction is conducted in an organic solvent which is miscible with water. It is preferable that the solvent used is also a solvent for the complex, since complex formation in solution and crystallization of the complex from solution provides pure crystals of the complex.

Use ful solvents include the aliphatic glycols and their mono-and diethers, e.g. ethylene glycol, monomethyl, monoethyl-, dimethyl- and diethylethers thereof, diethylene glycol and its mono- and dimethyl and mono- and diethylethers, and similar solvents. 1,2-Dimethoxyethane is a useful solvent.

The complex forming reaction is conducted by heating, preferably at reflux, the o-hydroxythiocyanate with a stoichiometric amount of the metal, e.g. nickel chloride, and a stoichiometric excess of a strong mineral acid, such as dilute HCl, HBr, $H_2SO_4$, etc. A base is then added to the reaction mixture in excess to liberate ammonia and then the base neutralized with an acid such as acetic acid.

EXAMPLE 1

A. Preparation of 5-Hydroxy-6-Benzo[c]Phenanthrenethiocyanate

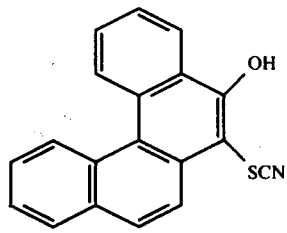

A stirred solution of 2.22 g. (0.0099 mole) of 5-hydroxybenzo[c]phenanthrene and 2.4 g. (0.02 mole) of sodium thiocyanate in 58 ml. glacial acetic acid was cooled in an ice water bath, then treated slowly with a solution of 1.59 g. (0.01 mole) of bromine in 6 ml. glacial acetic acid. The solid which precipitated was pale yellow. The entire reaction mixture was diluted with 350 ml. Water, the solid product collected on a filter, washed with water and air dried. The yield was 2.55 g. (85.5%), softening at about 98° C. and slowly melting up to 130° C.

B. Preparation of the Nickle Complex of 5-Hydroxy-6-Thiobenzo[c]phenanthrene

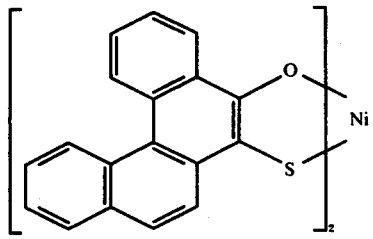

A stirred mixture of 2 g. (0.00665 mole) of the 5-hydroxy-6-benzo[c]phenanthrenethiocyanate from A (above), 0.95 g. (0.004 mole) of nickel chloride hexahydrate, 40 ml. of 1,2-dimethoxyethane, 5 ml. conc. hydrochloric acid and 10 ml. water was heated at refluxing temperature of 15 minutes. To this refluxing mixture there was added 10 g. of 50% sodium hydroxide. The resulting reddish-orange mixture was stirred for an additional 15 minutes at refluxing temperature and then 15 ml. water added. To this mixture there was added, dropwise and slowly, 9 ml. glacial acetic acid. About 30 ml. of the 1,2-dimethoxyethane was distilled off; a black crystalline complex separated from the reaction mixture. This product was collected on a filter, washed with water, then benzene, and dried. There was obtained 2.02 g. (100% yield) of the titled compound.

EXAMPLE 2

A. Preparation of 2,3-Dimethoxy-9-Hydroxy-10-Phenanthrenethiocyanate

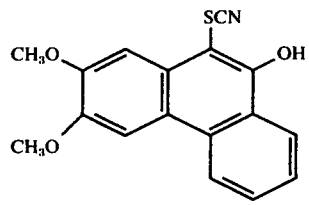

A stirred mixture of 2.6 grams (0.01 mole) crude 2,3-dimethoxy-9-phenanthrol in 80 ml. glacial acetic acid containing 2.4 grams (0.03 mole) sodium thiocyanate was heated to 70° C., cooled to 20° C., and filtered to remove 1.11 grams of an insoluble substance. The filtrate was held at 20° C. and treated slowly with a solution of 1.59 grams (0.01 mole) of bromine in 8 ml. acetic acid. This was stirred for about 30 minutes, the reddish-brown precipitate collected on a filter, washed with acetic acid, water and then air dried to give 0.85 gram. The filtrate as diluted with 300 ml. water, the precipitate filtered, washed with water, air dried and combined with the previous 0.85 gram to a combined yield of 1.93 grams (62%).

B. Preparation of Nickel Complex of 2,3-Dimethoxy-9-Hydroxy-10-Mercaptophenanthrene

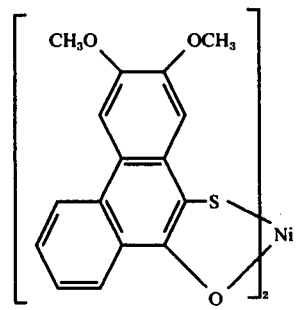

A stirred mixture of 1.08 grams (0.0035 mole) of 2,3-dimethoxy-9-hydroxy-10-phenanthrenethiocyanate from A (above), 0.95 gram (0.004 mole) of nickel chloride hexehydrate, 40 ml. 1,2-dimethoxyethane, 5 ml. conc. HCl and 10 ml. water was heated at reflux for about 15 minutes. To the refluxing mixture is added, slowly and dropwise, 10 grams of 50% caustic. The resulting reddish-brown mixture was stirred an additional 15 minutes at reflux and 15 ml. water added, followed by the slow addition of 9 ml. glacial acetic acid. About 30 ml. of the 1,2-dimethoxyethane was distilled off, the remaining suspension of dark, crystalline complex diluted with 40 ml. water, filtered, washed with water and air dried. There was obtained 1.05 grams desired product.

EXAMPLE 3

A. Preparation of 9-Hydroxy-10-Phenanthrenethiocyanate

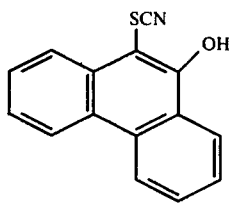

Following the procedure of Example 1(A) using 1.94 grams (0.01 mole) 9-phenanthrol, 2.4 grams (0.03 mole) sodium thiocyanate, 1.59 grams bromine and 100 ml. glacial acetic acid, there was obtained 2.45 grams (97.4%) of 9-hydroxy-10-phenanthrenethiocyanate.

B. Preparation of Cobalt Complex of 9-Hydroxy-10-Mercaptophenthrenethiocyanate

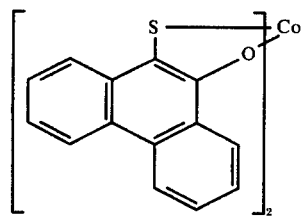

Following the procedure of the Example 1(B) using 1.31 grams (0.0052 mole) 9-hydroxy-10-phenanthrenethiocyanate from A (above), 0.72 gram (0.003 mole) cobalt chloride hexahydrate, 40 ml. 1,2-dimethoxyethane, 5 ml. conc. HCl, 10 ml. water, 10 grams 50% caustic and 9 ml. acetic acid, there was obtained 1.32 grams (100%) of the title complex.

I claim:

1. A method for the preparation of a transition metal complex of an aromatic o-hydroxymercaptan represented by the formula:

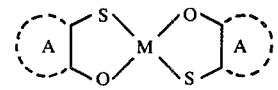

wherein M is a transition metal and A represents a mono- or polynuclear aromatic ring system, which comprises reacting an aromatic ortho-hydroxythiocyanate with an essentially stoichiometric amount of a water-soluble transition metal salt in a water-miscible organic solvent in the presence of a strong mineral acid.

2. The method of claim 1 wherein said transition metal is selected from the group consisting of titanium, chromium, manganese, iron, cobalt, nickel, cooper, zinc, cadmium, lead, silver, mercury and platinum.

3. The method of claim 1 wherein the aromatic ortho-hydroxythiocyanate if 5-hydroxy-6-benzo[c]-phenanthrenethiocyanate.

4. The method of claim 3 wherein the transition metal salt is nickel chloride.

5. The method of claim 1 wherein the aromatic ortho-hydroxythiocyanate is 2,3-dimethoxy-9-hydroxy-10-phenanthrenethiocyanate.

6. The method of claim 5 wherein the transition metal salt is nickel chloride.

7. The method of claim 1 wherein the aromatic ortho-hydroxythiocyanate is 9-hydroxy-10-phenanthrenethiocyanate.

8. The method of claim 7 wherein the transition metal salt is cobalt chloride.

9. The method of claim 1 wherein said solvent is selected from aliphatic glycols and their mono- and di-(lower alkyl)ethers.

* * * * *